United States Patent [19]

Dietz

[11] Patent Number: 5,052,400
[45] Date of Patent: Oct. 1, 1991

[54] METHOD AND APPARATUS FOR USING AN INHALATION SENSOR FOR MONITORING AND FOR INHALATION THERAPY

[76] Inventor: Henry G. Dietz, 80 Salisbury Ave., Garden City, N.Y. 11530

[21] Appl. No.: 262,485

[22] Filed: Oct. 25, 1988

Related U.S. Application Data

[63] Continuation of Ser. No. 831,181, Feb. 20, 1986, abandoned.

[51] Int. Cl.$^5$ .............................................. A61B 5/08
[52] U.S. Cl. ................................ 128/722; 128/204.26
[58] Field of Search ............... 128/716, 721, 722, 727, 128/725, 204.18, 204.21, 204.23, 204.26; 73/718, 724

[56] References Cited

U.S. PATENT DOCUMENTS

| | | | |
|---|---|---|---|
| 4,519,387 | 5/1985 | Durkan et al. | 128/204.23 |
| 4,686,975 | 8/1987 | Naimon et al. | 128/204.23 |

Primary Examiner—Lee S. Cohen
Assistant Examiner—J. P. Lacyk

[57] ABSTRACT

An inhalation sensor which uses a non-metallic diaphragm that is metallized on one side, pre-stressed, and used as one plate of a variable capacitance pressure tranducer to sense the inhalation and exhalation of air from the nostrils and/or mouth of a patient. The inhalation sensor is used for inhalation therapy by triggering a prescribed dose of therapeutic gas when inhalation takes place. The inhalation sensor can also be used as a monitor to detect apnea (the absence of breathing).

2 Claims, 4 Drawing Sheets

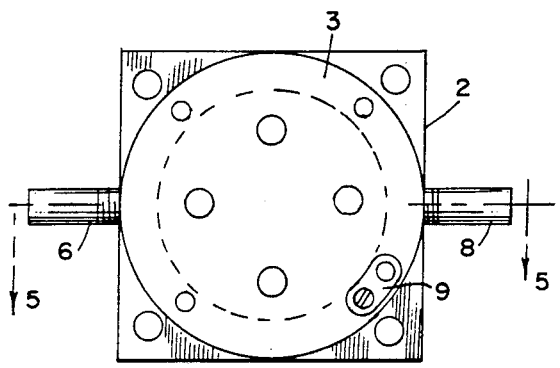
FIG. 1
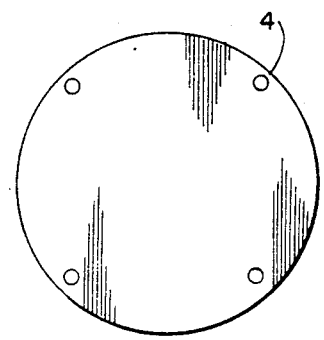
FIG. 4
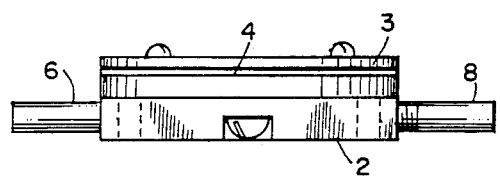
FIG. 2
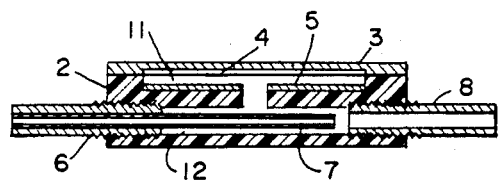
FIG. 5
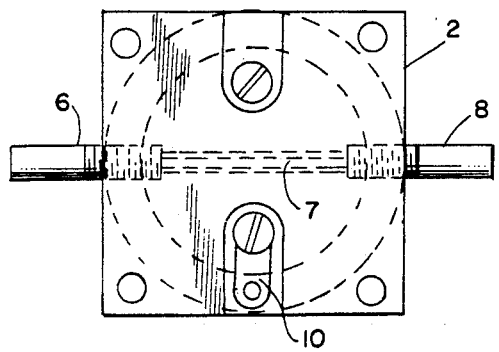
FIG. 3
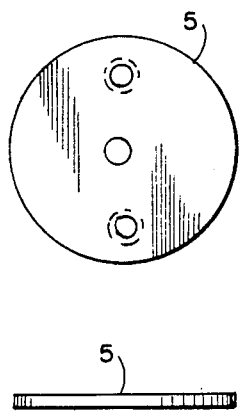
FIG. 6A
FIG. 6

METHOD AND APPARATUS FOR USING AN INHALATION SENSOR FOR MONITORING AND FOR INHALATION THERAPY

This is a continuation of application Ser. No. 831,181 filed on Feb. 20, 1986, now abandoned.

BACKGROUND OF THE INVENTION

This invention pertains to using an inhalation sensor for inhalation therapy and monitoring, and particularly using it with such apparatus and operating methods which features the triggering of a prescribed dose of therapeutic gas when inhalation takes place and/or detects when apnea (the absence of breathing) occurs.

There is an abundance of technology available for apnea detection. Apnea monitors using transthoracic impedance (requiring electrodes to be positioned on the chest) is presently the technique of choice for infants (ninety percent) and in adults (fifty percent), but it suffers from a fundamental deficiency: it provides a measure of thoracic effort rather than specific airway opening and patency.

The inhalation sensor, when used as an apnea monitor, overcomes this problem as it is measuring air flow at an airway opening such as the nasal openings or, if necessary, at the mouth.

The inhalation sensor must be capable of detecting movement of air at, or near, the mouth or nose. Thermistor temperature sensors can detect such air flow by detecting the cooling of a heated element. Air flow sensors are also marketed by such companies as the Micro Switch Division of Honeywell, and work on detecting air flow by cooling a heated element.

However, the problem with these devices is that they can not detect the direction of air flow and are incapable of indicating if the air is flowing in or out of the nose, and therefore, are not suitable for use as an inhalation sensor.

Pressure transducers that can detect extremely low pressures of 0.001 ounce per square inch and which are capable of detecting the vacuum created by inhalation and the pressure of exhalation, make excellent inhalation sensors. At the present time, semiconductor pressure transducers are of very low cost but are not capable of detecting negative and positive pressures of 0.001 ounce per square inch.

Pressure transducers designed for detection of such low pressures are often of the variable capacitance type as manufactured by MKS Instruments, Inc. of Burlington, Mass. . These transducers are all metal and are of high cost.

The lack of low cost air flow detection devices which use electric circuits has resulted in the use of fluidic devices to detect inhalation air flow.

In this regard, U.S. Pat. No. 4,457,303 to Durkon discusses the prior art and discloses the use of fluidics to obtain a device capable of detecting a negative pressure as small as 0.5 millimeters of water (approximately 0.01 ounce per square inch) by using a number of stages of fluidic amplification.

The applicant's inhalation sensor is capable of detecting negative pressure of 0.001 ounce per square inch by using a low cost non-metallic, metal-coated on one side diaphragm, variable capacitance type of pressure transducer, that is ten times more sensitive than the fluidic device described by Durkon.

A fundamental limitation to the application of pressure sensing or air flow detection by an inhalation sensor is keeping the inhalation sensor aligned with the airway exchange.

The applicant deals with this recognized difficulty by using the nasal cannula (which is an accepted method of administering oxygen for inhalation therapy) as a means of connecting a patient to the inhalation sensor.

Therefore, the physical positioning of the inhalation sensor is not important.

Often a patient, receiving oxygen via a cannula, will not have both prongs of the cannula properly aligned, and therefore, will not be receiving the benefits of the prescribed treatment. When this happens, the applicant's inhalation sensor can act as a monitor and sound an alarm and/or send a continuous flow of oxygen instead of a triggered dose.

The applicant's inhalation sensor, when used for inhalation therapy, supplies a dose of therapeutic gas each time a patient inhales. This means that since a patient inhales approximately 30% of the time, a possible saving of 70% of the oxygen used in a continuous flow system, can be saved. It also makes possible a greater volume of oxygen at an early stage of inspiration, and is more effective than conventional continuous flow because oxygen applied during the later stage of inspiration remains in "dead spaces" such as the pharynx, trachea, and bronchial tube. Oxygen given in the early stage of inspiration is most effective in reaching the alveoli.

This not only reduces the cost of oxygen, but eliminates a potential hazard by not having the 70% wasted oxygen being present in the environment.

If a patient breaths by shifting from nose to mouth, the cannula is replaced with a mouth/nose mask.

In prior art, two prongs were connected to two separate tubes, with one prong in one nasal opening being used as the sensor and the second prong placed in the other nasal opening, to supply the inhalation therapy gas.

The applicant's device requires only a single tube connected to the two prongs to serve as a sensor and supply the therapeutic gas.

The applicant's inhalation sensor requires no electrical connections to be made to a patient, and its electrical circuits can be made intrinsically safe (a device incapable of causing ignition of a flammable gas being used for inhalation therapy) because it is able to use low current and voltage for its operation.

SUMMARY OF THE INVENTION

This invention relates to an inhalation sensor that monitors the inhalation and exhalation of air from the nostrils and/or mouth of a patient, and more particularly, to a sensor that is actuated by a pressure as little as 0.001 ounce per square inch.

A principal object of this invention is to provide an inhalation sensor which can be used for inhalation therapy and apnea monitoring.

Another principal object of this invention is that the inhalation sensor be capable of being manufactured at very low cost by the use of a non-metallic diaphragm that is metallized on one side, pre-stressed, and used as one plate of a variable capacitance pressure transducer.

Another principal object of this invention is that the everyday nasal cannula used in hospitals for administering oxygen to a patient is the means for connecting the patient's nasal airflow to the inhalation sensor. If a patient breaths by shifting from nose to mouth, the cannula would be replaced with a mouth/nose mask.

Another principal object of this invention is to use the cannula connected to a patient's nostrils to sense inspiration and also to supply doses of therapeutic gases or aerosols to a patient via the same cannula.

Another principal object of this invention is that fluid or moisture that is trapped in this inhalation sensor can be easily removed by means of a built in venturi that develops a suction for removal of the fluid or moisture.

Another principal object of this invention is that the inhalation sensor be actuated by a pressure as low as 0.001 ounce per square inch and be capable of withstanding a high pressure of one pound per square inch without damage or loss of calibration.

Another principal object of this invention is that the inhalation sensor have no electrical connections to a patient, requiring only a single tube to be connected between sensor and patient. It is a passive device that incurs no hazards which can be associated with an electrical circuit.

Another principal object of this invention is that the employment of low current and voltage makes possible an intrinsically safe design of this device so it can be used with flammable therapeutic gases.

Another principal object of this invention is that the position of the inhalation sensor is not critical, since it is connected to a patient by means of a tube to a nasal cannula or a mouth/nose mask which can be aligned with the airway exchange.

Another principal object of this invention is that the inhalation sensor can be used for inhalation therapy. The inhalation sensor can supply a dose of therapeutic gas each time a patient inhales. This means that since a patient inhales approximately 30% of the time, a possible saving of 70% of the oxygen used in a continuous flow system can be obtained. It also makes possible a greater volume of oxygen at an early stage of inspiration, and is more effective than conventional continuous flow because oxygen applied during the later stages of inspiration remains in "dead spaces" such as the pharynx, trachea, and bronchial tubes. Oxygen given in the early stage of inspiration is most effective in reaching the alveoli.

Another principal object of this invention is to reduce the potential hazard resulting from oxygen of continuous flow system not being absorbed by a patient and being present in the environment.

Another principal object of this invention is to make possible such efficient use of oxygen that patients can use small portable oxygen tanks for greater freedom.

Another principal object of this invention is that a filter is inserted in the gas supply being inhaled into a patient's lungs to prevent any foreign object which may be present, being inhaled.

Another principal object of this invention is that a preset time for gas flow can be adjusted to match the breaths per minute for babies and adults.

Another principal object of this invention is that a capacitance switch sends an electrical signal when a patient's act of inhalation is detected by the variable capacitance of the inhalation sensor.

Another principal object of this invention is that the inhalation sensor can be used to monitor breathing by using a missing pulse detector. If no incoming pulse arrives from the act of inhaling before a pre-set timing period occurs, an alarm is activated to detect apnea.

Another principal object of this invention is that the number of apnea events can be counted to diagnose obstructed sleep apnea.

Another principal object of this invention is when a patient is receiving inhalation therapy, an alarm will indicate if the cannula becomes dislodged or if apnea occurs.

Another principal object of this invention is that when the inhalation sensor detects apnea, a full continuous flow of gas can be supplied to the patient.

Another principal object of this invention is to provide intermittent gas or aerosol flow to reduce the high cost involved in supplying a patient with continuous flow.

Another principal object of this invention is to provide an electrical signal which can be sent to a remote computer so that inexpensive constant surveillance of a patient's breathing pattern, with apnea detection, independently settable alarms, real-time graphics monitor display, and various other features can be obtained. This would provide inexpensive constant surveillance with signaling for intervention to reduce avoidable deaths.

Another principal object of this invention is to detect upper air passageway obstructions. Currently available monitors are dependent on impedance pneumography and heart rate indications. Such devices can not immediately detect obstructions in the upper air passageways. Inhalation sensors detect nasal and/or mouth airflow and, therefore, give immediate detection.

Still another principal object of this invention is to detect when a patient stops breathing and approaches death. Monitoring would detect patients who might lapse into a coma due to the hazards of reaction to or side effects of drugs. Detection of apnea in infants might prevent deaths due to sudden infant death syndrome.

DETAILED DESCRIPTION OF THE DRAWINGS

FIG. 1 is a top view of the inhalation sensor according to the invention.

FIG. 2 is a front elevation view of the inhalation sensor according to the invention.

FIG. 3 is bottom view of the inhalation sensor according to the invention.

FIG. 4 is a top view of the metallized film diaphragm according to the invention.

FIG. 5 is a section taken along section line 1—1 of FIG. 1.

FIG. 6 is a top view and front elevation view of the metal disc according to the invention.

DESCRIPTION OF THE PREFERRED EMBODIMENT

Figure 7:
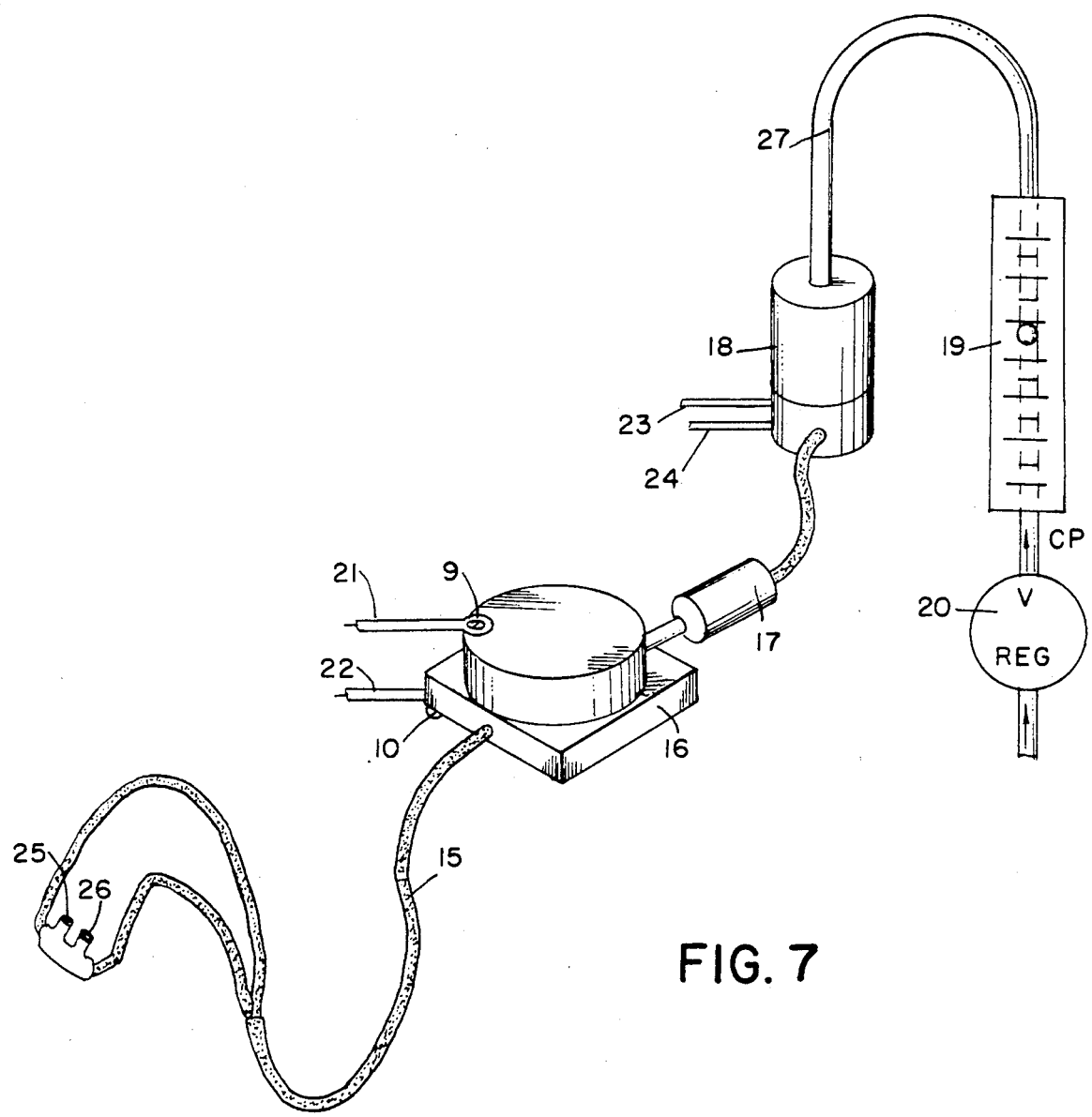
FIG. 7 is a diagrammatic view using an inhalation sensor for inhalation therapy in isometric projection.

FIG. 1, 2, and 3 generally illustrate a preferred embodiment of an inhalation sensor which comprises a square housing 2, made of a rectangular electrical nonconductor in cross section FIG. 5, having a central cavity 11 therein, the square housing 2 having an inlet connection 6, through one end, thereof, with a fitted internal tube 7, in passageway 12, and another outlet connection 8, through the other end of the square housing, both inlet and outlet passages being in direct communication with the central cavity 11 through the square housing.

With the flow of gas into the inlet connection 6, internal tube 7 with outlet connection 8 creates a venturi or eductor that develops a suction in central cavity 11. This suction is used to clear out any moisture that may have been entrapped in central cavity 11, which if not removed, could affect operation of the sensor.

The central cavity 11 is recessed to accept the metal disc 5 which forms one plate of a capacitor, and restricts the movement of the metallized film diaphragm 4 to prevent over-stressing. The metallized film diaphragm 4 is metallized on one side only. The non-metallized side facing metal disc 5. The metallized film diaphragm 4 can be 0.0005 inch thick polyester film coated on one side via vacuum metallization with aluminum or other equally suitable coated flexible material.

The metallized film diaphragm 4 is pre-stressed circumferentially and bonded to the outside surface of the square housing 2 with the stress maintained. The metallized film diaphragm 4 is sealed circumferentially to the square housing 2 forming a space between the metal disc 5 and the metallized film diaphragm. This space changes distance when a patient inhales, becoming smaller when inhalation takes place. However, with a maximum inhalation, the metallized film diaphragm 4 will actually contact the metal disc 5 and the lesser surface area of the metallized film diaphragm 4, thereby changing the electrical capacitance of the system. The maximum electrical capacitance is obtained when the only space between the metal disc 5 and the metallized surface of the metallized film diaphragm 4 is the polyester film. Electrical connection to metal disc 5 is made by lug 10 that is connected to disc 5 with a screw. Electrical connection to the metallized coating of the metallized film diaphragm 4 is made by metal clamping disc 3 which is fastened to the square housing 2 by a plurality of screws. The metal clamping disc 3 has a circular recess forming a cavity that is vented to outside atmospheric pressure.

Lug 9 makes electrical connection to the metallized surface of the metallized film diaphragm 4 by using one of the fastening screws. Minimum electrical capacity is obtained when gas is triggered and a positive pressure pushes the metallized film diaphragm 4 into the recess of the metal clamping disc 3. At the completion of a set time interval in which the triggered gas flows, the metallized film diaphragm 4 will go back to its unactivated pre-stressed state. If there is exhalation pressure available from the patient or therapeutic gas flowing, the electrical capacity will be minimum. Maximum electrical capacity is present only when the patient is inhaling.

FIG. 7 shows one method and apparatus for using an inhalation sensor for inhalation therapy. A cannula 15, commonly available in all hospitals for administering oxygen, is used to connect the flow of air from a patient's nostrils to the inhalation sensor 16 described above, by using the outlet connection 8, FIG. 1.

The filter 17 can be placed as shown on FIG. 7 or inserted between the cannula 15 and inhalation sensor 16. Its purpose is to prevent any foreign object that might be present in the gas supply being inhaled into the patient's lungs.

The inhalation sensor 16 is connected to the normally open solenoid valve 18 by means of appropriate tubing using the inlet connection 6 of the inhalation sensor 16. The solenoid valve 18 is electrically actuated by low voltage and low current that can be supplied by an electronic circuit that can be designed to be intrinsically safe (a circuit that is incapable of having a spark or thermal effect that would be capable of causing ignition of a flammable or combustible material in the gas being used for inhalation therapy). The tube 27 is used to connect the solenoid valve 18 to the supply of gas being used for therapy. In hospitals, the flow meter 19 and the pressure regulator 20 would be usually available at the patient's bedside and supply a constant flow of gas (such as 0 to 10 liters of oxygen per minute). Present day practice is for hospitals to have oxygen piped permanently into each room used for patients' care.

For home use where oxygen is delivered in tanks, the apparatus supplied with such tanks include some type of flow gage such as the flow meter 19 and the pressure regulator 20.

The cannula 15 is adjusted to fit the patient, so that the two prongs 25 and 26 are inserted into the patient's nostrils. The flow of air from the patient's nostrils produces a very low pressure or vacuum at the end connected to the inhalation sensor 16.

The vacuum pressure produced by the patient inhaling is no more than a few thousands of an ounce per square inch. At the time the patient is exhaling, the electric solenoid valve is electrically activated and shuts off the flow of gas from the therapeutic gas being used. When the patient inhales, the metallized film diaphragm 4 is sucked down so that its metallized coatings is at a minimum distance from the metal disc 5 and the output at lugs 9 and 10 of the inhalation sensor 16 exhibit maximum electrical capacitance. Lugs 9 and 10 are respectively connected to wires 21 and 22. With appropriate electrical circuits as described in this patent specification, a signal is sent for a pre-determined time to cause a flow of therapeutic gas by electrically deactuating the normally open valve 18. In actual practice, it has been found that the flow of air being sucked in by the patient is at a maximum for only a very short period of time, and this peak flow of air vacuum from the patient's nostrils, is used to trigger the flow of the therapeutic gas for a pre-set time.

The length of the pre-set time can be adjusted for the correct flow of therapeutic gas for the normal adult rate of 14 to 20 breaths per minute, or for 20 to 40 breaths for babies and toddlers. The respiration rate rises as much as four breaths per minute for every degree of temperature over normal.

The pre-determined time therefore, provides for an intermittent flow of therapeutic gas to the patient. The patient normally inhales approximately for 30% of the time for each breath with 70% of the breath for exhaling. By setting the pre-set time to 30% of the breath time, a savings of 70% of the therapeutic gas can be achieved over the normal hospital system of having a constant flow. It is also possible to apply the therapeutic gas at the very early stage of inspiration with a large volume of gas which will reach the alveoli and not waste additional gas that remains in the "dead spaces" such as the pharynx, trachea, and bronchial tubes.

At the time the therapeutic gas flows into the inhalation sensor 16 high pressure is applied to the metallized film diaphragm 4, causing it to be in close contact with the metal clamping disc 3 for minimum electrical capacitance at lugs 9 and 10. Therefore, upon completion of the pre-set time, a signal is sent by the inhalation sensor 4, to an electrical circuit that actuates the solenoid valve 18 to its closed position and shuts off the flow of therapeutic gas to the inhalation sensor 16 and the cannula 15.

Upon completion of the patient's exhaling, the cycle of events will be repeated by the patient again inhaling.

Figure 8:
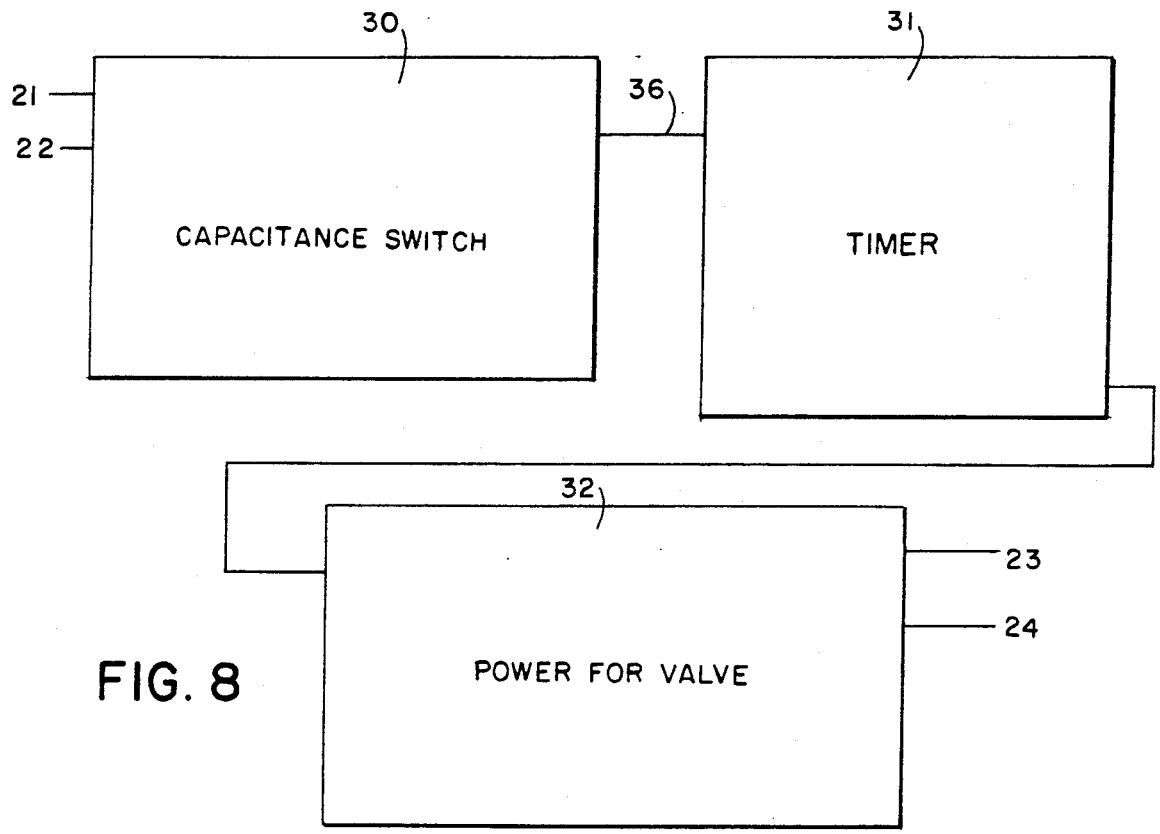
FIG. 8 is a block diagram of the method of using an inhalation sensor for inhalation therapy according to the invention.

FIG. 8 generally illustrates one of the preferred means of devices used to obtain intermittent flow of the therapeutic gas. The inhalation sensor 16 is connected to the capacitance switch 30 FIG. 8 which sends an electrical signal to the timer 31 when the patient inhales. The electrical signal from the capacitance switch 30, actuates the timer to send a signal to the power circuit for the solenoid valve 32 for a pre-determined time.

The power circuit for the solenoid valve 32 will deactuate the solenoid valve 18 for the pre-determined time. At the end of the pre-determined time the power circuit for the solenoid valve 32 will actuate the solenoid valve and the therapeutic flow of gas will stop. When the flow of therapeutic gas is stopped, the inhalation sensor 16 will again respond to inhalation air flow from the patient's nostrils, supplied by the cannula 15.

Figure 10:
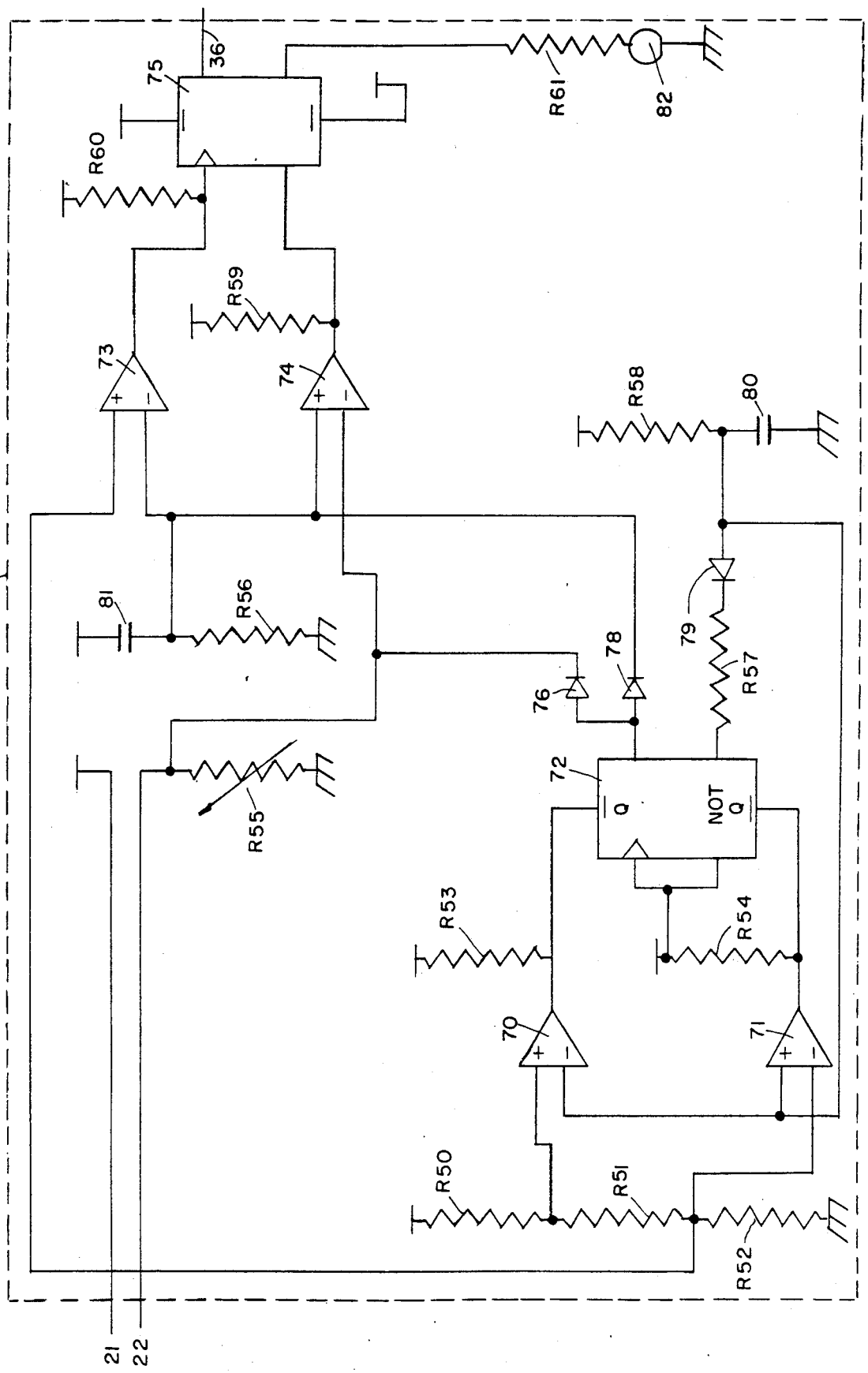
FIG. 10 is a schematic diagram of the electrical circuit of the capacitance switch according to the invention.

The capacitance switch 30, consists of the electrical circuit shown in FIG. 10. The electrical circuit must detect when the capacitance of the inhalation sensor exceeds a certain preset limit, and report this event with a simple logic signal.

The operation of the circuit shown in FIG. 10 is quite straight forward. The inhalation sensor's capacitance at terminals 21 and 22 and the reference capacitor 81 are charged through resistors R55 and R56 respectively. Resistor R55 is made adjustable to trim capacitance mismatch. When the voltage across the reference capacitor 81 exceeds two thirds of the supply voltage as detected by comparator 73, the result of the comparison of the voltage level on the inhalation sensor's capacitance at terminal 21 and 22 and the reference capacitor 81 by comparator 74 is latched into the D-type flip-flop 75. The output 36 is thus determined by the relative values of resistor R55 multiplied by the capacitance of the inhalation sensor 16 and resistor R56 multiplied by the capacitance of the reference capacitor 81, assuming they start charging at approximately the same instant. A simple oscillator insures this by periodically discharging the inhalation sensor's capacitance at terminals 21 and 22 and the reference capacitor 81 through diodes 76 and 78, allowing the measurement to be updated.

The oscillator is a standard, conservative, self-starting design. Capacitor 80 charges through resistor R58 until the voltage across it reaches two thirds of the supply voltage. Comparator 70 detects this condition, and sets the flip-flop 72. This allows current to flow through resistor R57 and diode 79, discharging capacitor 80. When the voltage across this capacitor reaches one third of the supply voltage, the flip-flop 72 is reset by comparator 71, switching diode 79 off. Thus, the cycle begins again with capacitor 80 charging through resistor R58.

In order to discharge the capacitor 80 past one third of the supply voltage, resistor R58 must be at least twice as large as resistor R57. Thus, the resistor's R57 output is high most of the time. The inverted version of this signal is used to discharge the inhalation sensor capacitance terminals 21 and 22, and reference capacitor 81 in short bursts by forward biasing diodes 76 and 78. The logic swing of the flip-flop needs to be the full supply range in order for this circuit to function properly. Almost all of the CMOS logic families have this feature.

One of the main advantages of this circuit is its very low cost. Monolithic quad comparators are widely available, as are monolithic dual D-type flip-flops. The total parts count is low. Interfacing to more complicated logic functions is straight forward.

Figure 9:
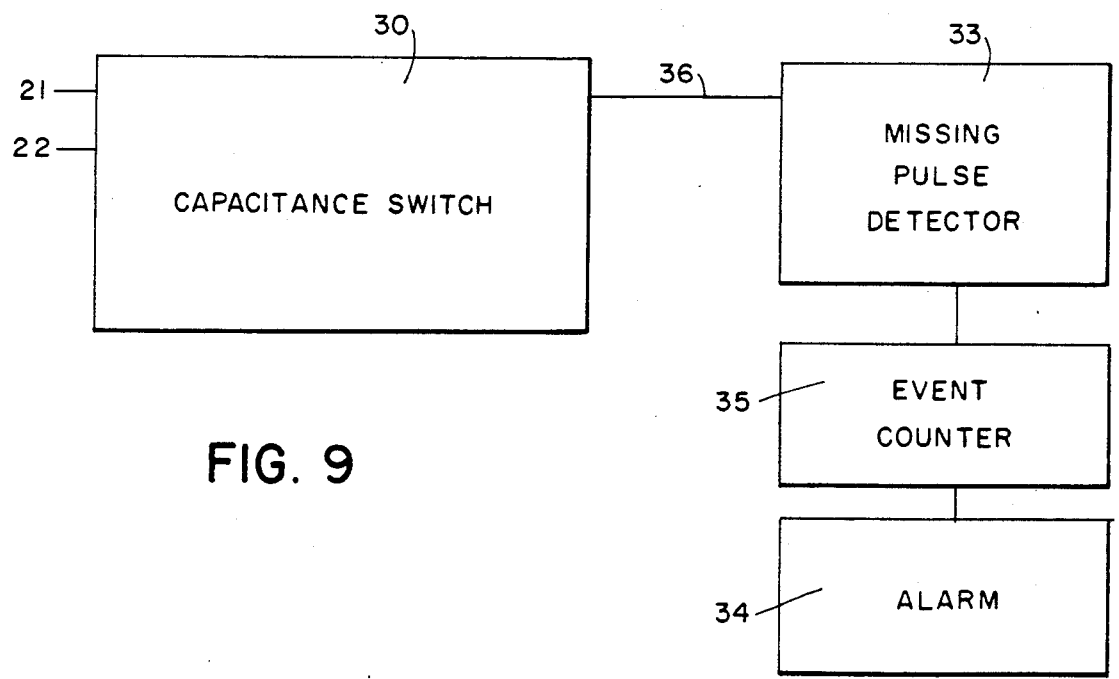
FIG. 9 is a block diagram of the method of using an inhalation sensor for monitoring according to the invention.

The inhalation sensor 16 can be used to monitor breathing as shown in FIG. 9, by using only one of the connections 6 or 8 and plugging the hole of the unused connector. The connection 6 or 8 should be used with the cannula 15. When the inhalation sensor is used for monitoring FIG. 9, the patient inhaling will produce the maximum electrical capacitance. The capacitance switch 30 will send an electrical pulse to the missing pulse detector 33 each time the patient inhales. As long as incoming pulses arrive before the set timing period of the missing pulse detector 33 runs out, no signal will be sent to event counter 35 and alarm 34. However, if no incoming pulse arrives before the set timing period occurs, the event counter 35 and alarm 34 are activated.

As an added feature, an event counter 35 can count the number of times the alarm has been actuated.

The alarm 34 will be actuated each time the patient dislodges the cannula and the cannula is not sensing breathing, or if the patient experiences apnea (a cessation of breathing that lasts beyond the set timing of the missing pulse detector). This feature can be used to detect apnea in infants to prevent sudden infant death, and to provide constant surveillance of patients' breathing by sounding an alarm to obtain intervention to prevent avoidable death.

It is also possible to combine the functions of inhalation therapy with monitoring, by taking an electrical signal from terminal 23 of the solenoid valve 18 and connecting it to 36 of FIG. 9, using the missing pulse detector 33, alarm 34, and event counter 35. Doing this will signal an alarm when the cannula becomes dislodged from the patient's nose, when the patient experiences apnea, and if the solenoid should become inoperative. It also will count each time the events occur.

It is also possible to have a continuous flow of oxygen each time the alarm is energized by connecting the output of the alarm 34 to deactuate the solenoid valve 18.

While the invention has been particularly shown and described with references to the preferred embodiments thereof, it will be understood by those skilled in the art that various alterations in form and detail may be made therein without departing from the spirit and scope of the invention. Moreover, while the invention has been particularly shown and described for clinical use (as with a patient for example), it should be understood the invention may be used in conjunction with gas supply or apnea detection in a subject in industrial, aeronautical, subterranean or underwater environments.

The embodiments of the invention in which an exclusive property or privilege is claimed are defined as follows.

I claim:

1. An apparatus for sensing the breathing of a human and for inhalation therapy, comprising:
    a pressure capacitance transducer for developing pressure variations internally of the pressure capacitance transducer in response to the breathing of said human,
    a supply of therapeutic gas, said transducer having an inlet connected to said supply of therapeutic gas and an outlet adapted for connection to the respiratory system of said human for developing a negative pressure, sensing means internally of said pressure capacitance transducer for sensing each time a negative pressure occurs internally of the pressure capacitance transducer corresponding to the inhalation of said human, means responsive to said sensing means for developing individual electrical signals in response to the sensing of each said negative pressure, timing means co-acting with said individual electrical signals for controlling predetermined periods of therapeutic gas flow through said pressure capacitance transducer to the respiratory system of said human, said gas flow being interrupted in the absence of said electrical signals, filtering means connected between said gas supply and said pressure capacitance transducer for filtering said therapeutic gas, said pressure capacitance transducer further comprising an eductor means for removing moisture from internally of said transducer, said eductor means being a tube having an inlet connected to said transducer inlet and an outlet disposed internally of said transducer and substantially aligned and separated from said transducer outlet for creating suction, thereby removing any moisture within said transducer.

2. An apparatus for sensing the breathing of a human and for inhalation therapy according to claim 1, further comprising:

a missing pulse detecting means having a preset timing period, said missing pulse detecting means responding to said individual electrical signals for continually retriggering said missing pulse detecting means, an alarm means connected to said missing pulse detecting means, whereby if said missing pulse detecting means fails to be retriggered within said preset timing period, said alarm means will sound.

* * * * *